(12) United States Patent
Kalayeh et al.

(10) Patent No.: US 6,822,742 B1
(45) Date of Patent: Nov. 23, 2004

(54) SYSTEM AND METHOD FOR REMOTE QUANTITATIVE DETECTION OF FLUID LEAKS FROM A NATURAL GAS OR OIL PIPELINE

(75) Inventors: Hooshmand M. Kalayeh, Pittsford, NY (US); Gustavo R. Paz-Pujalt, Rochester, NY (US); John P. Spoonhower, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 10/740,879

(22) Filed: Dec. 19, 2003

(51) Int. Cl.[7] .............................................. G01N 21/61
(52) U.S. Cl. .................. 356/437; 356/432; 250/339.11; 250/338.1; 73/335.01; 73/40.5 A
(58) Field of Search ................................ 356/432–444; 250/338.1, 339.1, 339.11, 339.05, 338.5; 73/335.01, 40.5 A, 592

(56) References Cited

U.S. PATENT DOCUMENTS

| | | | |
|---|---|---|---|
| 4,001,764 A | * 1/1977 | Holland et al. ................. 367/6 |
| 4,450,356 A | 5/1984 | Murray et al. ............... 250/339 |
| 4,489,239 A | 12/1984 | Grant et al. ................. 250/339 |
| 4,871,916 A | 10/1989 | Scott ........................ 250/338.5 |
| 5,166,789 A | * 11/1992 | Myrick ........................ 348/144 |
| 5,250,810 A | 10/1993 | Geiger .................... 250/338.5 |
| 5,410,154 A | * 4/1995 | Broicher et al. ....... 250/339.05 |
| 5,481,476 A | 1/1996 | Windig ....................... 364/498 |
| 5,818,951 A | * 10/1998 | Schivley ..................... 382/100 |
| 6,366,681 B1 | * 4/2002 | Hutchins .................... 382/110 |
| 6,509,566 B1 | 1/2003 | Wamsley et al. ........ 250/338.5 |
| 6,725,705 B1 | * 4/2004 | Huebler et al. .......... 73/40.5 A |

OTHER PUBLICATIONS

"Innovative Technologies Improve Environmental Protection—Detection of Gas Leaks by Helicopter–Borne Infrared Laser System" by Werner Zirnig and Matthias Ulbricht. pp. 1–7.

"Compact mid–infrared DIAL lidar for ground–based and airborne pipeline monitoring" by Egor V. Degtiarev, Allen R. Geiger, and Richard D. Richmond. Remote sensing of Clouds and the Atmosphere VII, Klaus Schäfer, Olga Lado–Bordowsky, Adolfo Comerón, Richard H. Picard, Editors. *Proceedings of SPIE* vol. 4882, 2003.

"High–Pressure Measuring Cell for Raman Spectroscopic Studies of Natural Gas" by S. Brunsgaard Hansen, R. W. Berg and E.H. Stenby. *Applied Spectroscopy*, vol. 55, No. 1, 2001, pp. 55–60.

* cited by examiner

*Primary Examiner*—Frank G. Font
*Assistant Examiner*—Sang H. Nguyen
(74) *Attorney, Agent, or Firm*—RatnerPrestia

(57) ABSTRACT

A system for remote quantitative detection of fluid leaks from a natural gas or oil pipeline by use of an airborne platform; including at least one laser light source for nearly simultaneous illuminating two or more target fluids and a background, wherein the two or more target fluids are characterized by two or more absorption wavelengths, and wherein the background has a different wavelength than either of the two or more target fluids. The illumination source is pointed based on a positioning system while in a geometric area along a path two or more target fluids are scanned for using the illumination sources. A signal detector detects the two or more target fluids using quantitative signal processing. Also included are a controller, a path planning and path finding tool for the positioning of the airborne platform, and a communicator for communicating the presence of the detected leak.

20 Claims, 11 Drawing Sheets

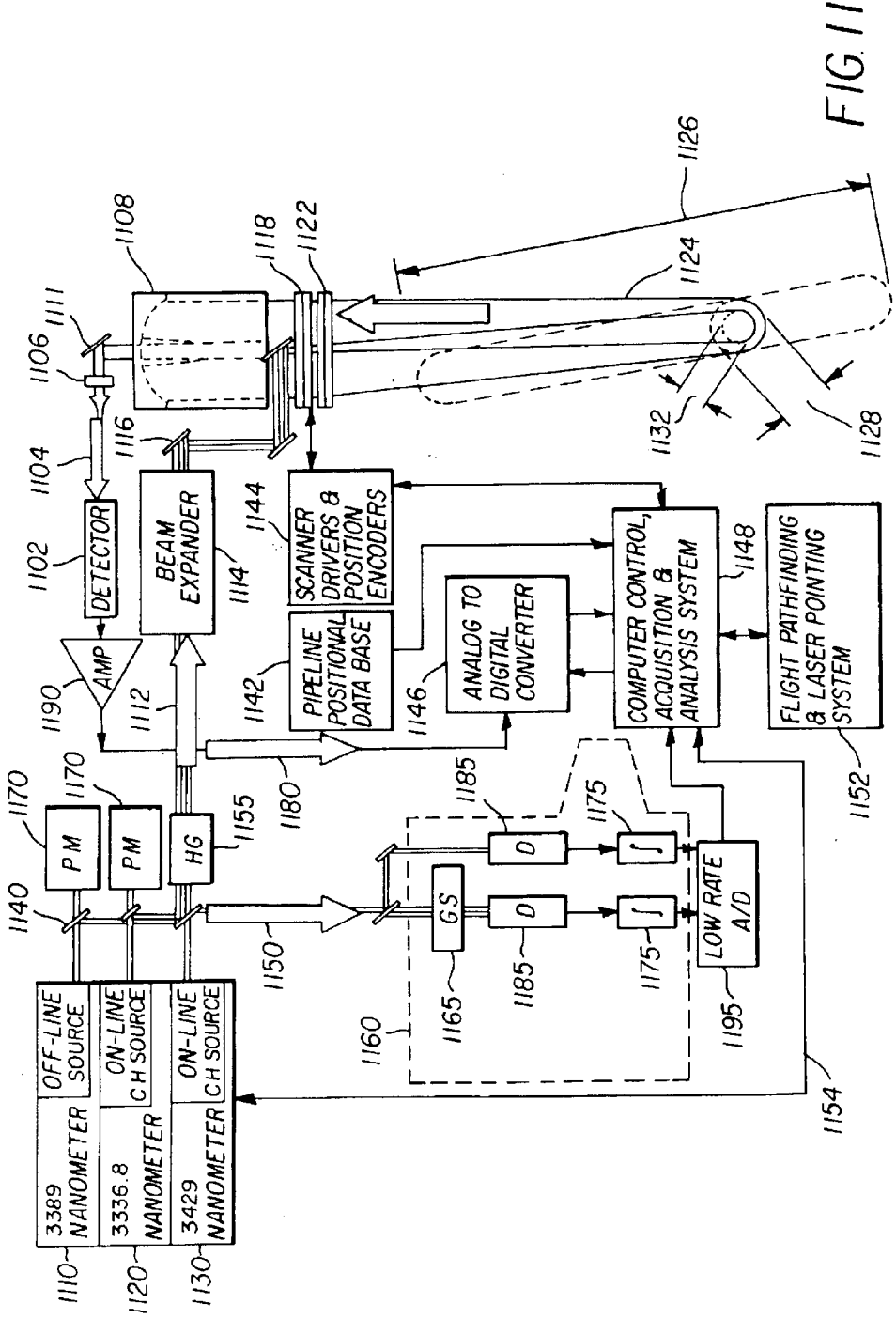

SYSTEM AND METHOD FOR REMOTE QUANTITATIVE DETECTION OF FLUID LEAKS FROM A NATURAL GAS OR OIL PIPELINE

FIELD OF THE INVENTION

The invention relates generally to the field of spectroscopic analysis. More specifically, the invention relates to a spectroscopic analysis of trace fluids emanating from natural gas and oil pipelines using laser differential absorption.

BACKGROUND OF THE INVENTION

Surveillance of ground topography is well known in the art. In ground surveillance, it is highly desirable to detect whether there has been a material failure in a man-made object such as a road, a pipeline, an electrical grid, or another man-made structure of practical interest. When a structural failure is detected, proper authorities make a determination whether remedial action is necessary. Often times a land-based crew conducts a visual inspection of the ground topography to determine if there is a material failure by traversing an area by vehicle or foot. It is frequently the case that an aircraft or a satellite includes an image capture device such as a charge coupled device (CCD), complementary metal oxide semiconductor device (CMOS) or a radiation detector, such as an infrared sensitive detector. It is well known that airborne photographic systems can also be used for capturing images of adjacent areas of the ground.

When electromagnetic radiation, interacts with matter several phenomena may occur, including scattering, absorption, transmission and reflection of the electromagnetic radiation. Spectral or spectroscopic analysis includes carefully examining, analyzing, and representing the interactions involving electromagnetic radiation and matter, in an orderly fashion, as a function of wavelength, frequency, or time. During spectroscopic analysis, different materials exhibit different scattering, absorption, reflection and transmission characteristics. These distinctive characteristics are determined by the chemical and physical structure of the materials. When a set of these distinctive characteristics are determined to a given level of certainty, as with the use of known test subjects, these spectroscopic results may be referred to as reference spectral signatures or reference spectra.

Natural gas, characteristically, contains a mixture of methane, ethane, and small amounts of other gases. Gas generated by the decomposition of organic matter, henceforth, referred to as swamp gas, only contains methane. It is highly desirable for any natural gas detection method to be able to distinguish between gases released as a result of a failure in a pipeline or a holding container versus emanating swamp gases, thus avoiding false alarms.

Oil pipelines contain significant concentrations of volatile dissolved gas compounds, including methane, ethane, and propane. Oil pipelines operate under pressure; leaks and a concomitant pressure drop result in escaping volatile components, and thereby provide a means for leak detection. Electromagnetic radiation can be directed onto a test subject by any of a variety of means. Commonly, lasers are used but other means such as the use of antennas for radio and microwave electromagnetic energy may be used. Hereafter, when electromagnetic radiation is directed onto a test subject it is referred to as an illuminant.

In detecting failures of gas and oil pipelines there is a particular problem, as the gas or oil pipeline is typically buried beneath ground level. In such cases, it is difficult to make a direct visual assessment of any failures in the pipeline. When failures do occur they are manifest by the leakage of the pipeline contents, the leaking material produces a characteristic trace or signal. Typically, failures in pipelines are currently determined by having personnel walk the pipeline on a periodic and costly basis with some means to detect the trace emanating from the pipeline. Gases can escape a pipeline and travel through subterranean earth to the earth's surface and then into the atmosphere. Consequently, the atmosphere can be monitored for gases that have escaped the pipeline. An association of gases detected in the atmosphere with a pipeline leak may be direct or indirect. An example of a direct association is the release of specific hydrocarbon gases to the atmosphere from subsurface oil and gas pipelines. Natural gas consists of 2 primary components, methane and ethane, with a fairly fixed proportion in a mixture. Measurement of both components and confirmation of the appropriate concentration ratio directly establishes the presence of a pipeline leak. In this case, association is direct in that the gas components themselves are emitted into the atmosphere, albeit with a potentially modified composition. Similarly, other volatile components of the contents of gas-bearing pipelines are detectable and will indicate the presence of a leak. Methane is produced from thermal or biological breakdown of coal. The gas detected (methane) is not the same as the natural resource (coal), so the term "indirect" is used to describe this association. The term "indirect association" does not imply that the scientific basis for the association is weak. The process of converting coal to methane is well described in the scientific literature.

For oil or petroleum pipelines, release of certain volatile components can indicate the presence of a fluid leak, and thus constitute indirect evidence of a pipeline failure. Laser absorption spectroscopy (LAS) is a sensitive means for quantifying molecular concentrations in a variety of situations not amenable to other techniques, particularly remote sensing applications. A main advantage of LAS is that the measurement is done "in situ"; this enables rapid measurements with good spatial resolution in a variety of environments. For an absorption experiment, the ratio of the transmitted beam intensity $I(v,x)$ to the initial beam intensity, $I_0(v,x=0)$, is related to an absorber concentration, n, by Beer's Law, $$I(v,x)/I_0(v,x=0)=e^{-n x \sigma(v)}.$$

The molecular cross-section at frequency, v, is denoted by $\sigma(v)$ and the path length over which the laser travels by x. For any given signal to noise ratio (SNR) for the measurement of $I(v,x)/I_0(v,x=0)$, the measurement sensitivity can be increased by increasing the path length. There are a number of prior art patents that include laser means for detecting trace gases in the atmosphere. Some of these laser-based systems operate in the microwave or the ultraviolet wavelength region. These laser-based systems are unlike the subject invention that operates in the mid-infrared wavelength range. The following patents are discussed since the laser-based systems described therein also operate in the mid-infrared wavelength region while detecting hydrocarbon gases.

In U.S. Pat. No. 4,450,356 issued to Murray et al., a frequency-mixed carbon dioxide ($CO_2$), laser beam is used for remote detection of gases in the atmosphere. The laser beam system uses frequency doubling and frequency summing in crystals to produce wavelengths near three micrometers. Means for selecting many wavelengths are disclosed, but delivery of only two mid-infrared wavelengths to a topographic target are disclosed. $CO_2$ lasers are continuously not tunable and lack strong lines at wavelengths coincidental with acceptable methane and ethane lines. In U.S. Pat. No. 4,489,239, a 25 meter short distance portable remote laser sensor is described for detecting methane gas pipeline leaks by Grant et al. The system requires the use of two separate helium-neon (He—Ne) lasers. The two lasers operate at two different on and off methane signature wavelengths, each of which is fixed. He-Ne lasers are typically not tunable and not as efficient and reliable as solid-state lasers. Similarly, In U.S. Patent Application Publication 2003/0030001 A1, Cooper et al disclose the use of a tunable diode laser to detect gases in the atmosphere. This system does not allow for real-time compensation for variability in the background target reflectivity and cannot measure multiple gas species nearly simultaneously, a critical requirement for scanning and remote sensing systems that detect pipeline leaks. In U.S. Pat. No. 4,871,916, a laser system is described by Scott that uses neodymium lasers for remote sensing of methane in the atmosphere to detect conditions approaching dangerous or explosive levels in a mine. In this system, the wavelength region is nearly at 1.318 micrometers. This system only discloses detection of methane and does not allow for real-time compensation for variability in the background target reflectivity. In U.S. Pat. Nos. 5,157,257 and 5,250,810 assigned to Geiger, a mid-infrared DIAL system is described. This specific system uses six distinct coherent beams formed by six different pulsed lasers at wavelengths 2.2 to 2.4 or 3.1 to 3.5 micrometers to detect light hydrocarbons. The six coherent beams are fully time-multiplexed and combined into a single beam through selective polarization. Quartz crystals are used for polarization. The quartz crystals are easily damaged by high-energy laser pulses and complexity of this system is not conducive to use in the field, particularly in airborne remote sensing applications. Also, the laser spectral width is too broad to resolve the absorption bands of many key gases. In U.S. Pat. No. 6,509,566 B1 assigned to Wamsley et al., a mid-infrared DIAL system is also described for the purposes of oil and gas exploration. The system disclosed includes a single Cr:LiSAF laser with a hydrogen Raman cell to produce wavelengths in a range suitable for hydrocarbon detection. The laser is water-cooled and continuously tunable at a single wavelength. This system does not conveniently allow for real-time compensation for variability in the background target reflectivity and simultaneous detection of other gases. Furthermore, the single laser frequency is referenced to an external frequency meter and is, therefore, subject to drift that negatively affects the electronic components in the system.

PROBLEM TO BE SOLVED BY THE INVENTION

It is understood that pipelines usually carry petroleum, or oil, natural gas, refined petroleum or gas products, chemicals, mineral ore slurries and other fluid or fluidized substances or mixtures. The aforementioned laser-based systems are unable to detect nearly simultaneously multiple gas species, such as methane and ethane that are found in natural gas pipelines. They also do not compensate for variations in the reflectivity of the background or target. Additionally, lasers that are not continuously tunable cannot be specifically tailored for detecting various gas species. False alarms continue to plague the above-mentioned prior art systems and their sensitivity to detecting multiple gas species is questionable. Other trace gases that arise in the atmosphere can also interfere with the detection of natural gas with these prior art laser-based systems.

SUMMARY OF THE INVENTION

The present invention is directed to overcoming one or more of the problems set forth above by providing a system for remote quantitative detection of fluid leaks from a natural gas or oil pipeline by use of an airborne platform that includes at least one laser light source for nearly simultaneous illuminating essentially a same target area of two or more target fluids and a background, wherein the two or more target fluids are characterized by two or more absorption wavelengths, and wherein the background is detected at a different wavelength than either of the two or more target fluids.

In addition, the present invention further includes a means for pointing the illumination source based on a positioning system; a means for scanning for the two or more target fluids in a geometric area along a path using the illumination source; a means for signal detection such that a quantitative processing of detection of the two or more target fluids is accomplished; and a means for controlling operation of the system. A signal processing means for the remote quantitative detection of the two or more target fluid leaks; and a means for path planning and path finding for the positioning of the airborne platform; as well as a means for communicating presence of the detected leak from the natural gas or oil pipeline are integral to the present invention.

ADVANTAGEOUS EFFECT OF THE INVENTION

The present invention has the following advantages: it utilizes a well-developed one-micron Diode Pumped Solid-State, Optical Parametric Oscillator and Optical Parametric Amplifier; it has reasonable wavelength conversion efficiency, it is capable of measuring multiple targets concentration pathlength as the surface cover type (background) changes; and it is continuously tunable.

BRIEF DESCRIPTION OF THE DRAWINGS

Referring to the drawings, components in FIG. 1 are labeled by numbers greater than 100 and less than 200, components in FIG. 2 labeled by numbers greater than 200 and less than 300, and so on.

FIG. 11 is a block diagram of the 3-line tunable DIAL laser fluid pipeline leak detection system. To facilitate understanding, identical reference numerals have been used, where possible, to designate identical elements that are common to the figures.

DETAILED DESCRIPTION OF THE INVENTION

Figure 1:
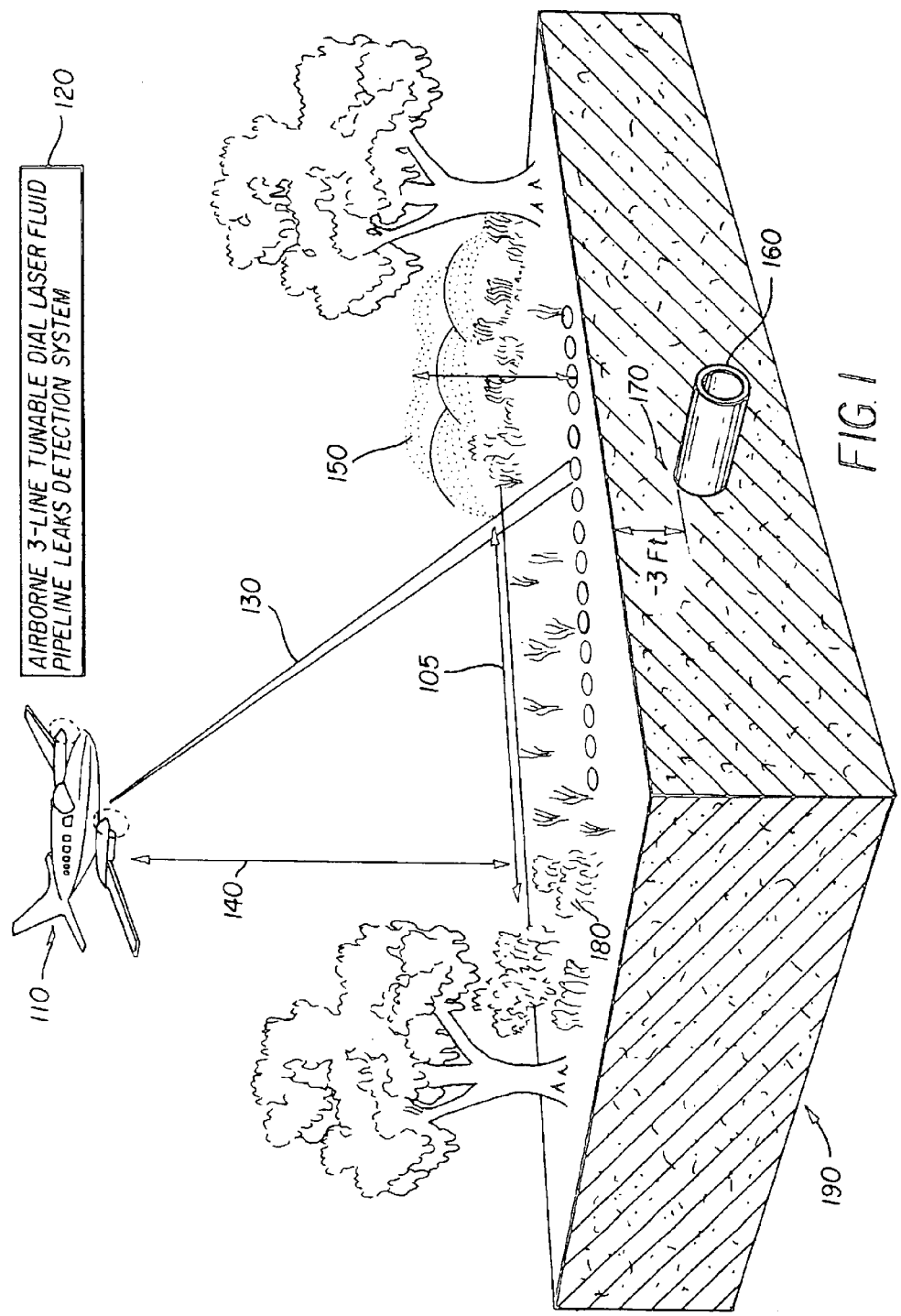
FIG. 1 is an exemplary schematic diagram of a 3-line tunable DIAL laser fluid pipeline leak detection system aboard a fast moving airborne platform according to the present invention.

The present invention described herein addresses the measurement of gases associated with oil and gas leakages from pipelines. This invention relates to an oil and gas pipeline leak detection system and method of detecting gases in the atmosphere and more particularly, but not by way of limitation, to detecting pipeline leaks based upon differential absorption lidar (DIAL) sensing techniques operating in a mid-infrared 2 to 5 micrometers, spectral range. In general, the following fluids may be detected or explored: gas, volatile oil, light crude oil, heavy crude oil, and hazardous. The gas concentrations are mapped over an area and the maps are analyzed for concentration anomalies. The gas anomalies are interpreted to evaluate the underground pipeline leak.

In the discussion of the present invention, the term "target fluids" is used to indicate fluids that are associated either directly or indirectly with pipeline leaks. Target fluids can mean either liquids or gases. The measured atmospheric concentrations of target fluids form the basis of the new infrastructure assessment tool as described herein. Target fluids must have some unique characteristics to their association with the pipeline leak. For example, methane is produced in a number of ways. It may occur in the atmosphere as a result of emission from a hydrocarbon deposit, emission from a coal deposit, emission from wetlands with active populations of methane producing bacteria, emission from a leaking natural gas pipeline, etc. Sources of methane other than a pipeline leak are said to be environmental interferences. Environmental interferences complicate the association between a target fluid and the pipeline leak; and will vary in magnitude and type with standard geological factors such as soil type, hydrology, subsurface structure and composition, as well as atmospheric conditions, weather and land use. A unique gas mixture such a methane/ethane is a useful target fluid for natural gas pipelines. Individual gases or gas combinations that have very unique associations with the pipeline leak provide the most valuable signals indicating the presence of a leak.

The present invention teaches the use of a differential absorption lidar (DIAL) that samples along a path through the atmosphere. A wide range of instruments have been developed which detect most trace gases in the atmosphere. These instruments can be loosely categorized as techniques that sample air at a specific point in space and remote sensing systems such as the numerous satellite- or aerial-based systems which provide large-scale measurements of gas concentrations. There are numerous types of gas sources that, because of their unique spatial and temporal properties, cannot be accurately characterized by these techniques. Monitoring emissions from such sources requires a system that can measure minute concentrations quickly and over long paths, remotely. Long path differential absorption lidars (DIALs) typically meet these requirements. One aspect of the present invention is to utilize an airborne platform-based 3-line tunable differential absorption lidar (DIAL) laser optical sensor for remote quantitative detection of leaks from a natural gas or oil pipeline. Another aspect of the present invention is to select the trace gases that optimally characterize fluid pipeline leaks. For the present invention, the gases released into the atmosphere from both gas and oil pipeline leaks are evaluated and methane and ethane are selected for robust detection of both types of leaks. Another aspect of the present invention optimally selects the molecular transition of the optical absorption characteristics of methane and ethane within the mid-infrared region of the electromagnetic spectrum. Methane and ethane absorption characteristics are analyzed and two on-wavelengths (also referred to as on-line) and one off-wavelength (also referred to as off-line) for the methane, ethane and the earth-surface type (background) respectively, are selected for the leak detection. The on-line wavelengths are selected close to the peak of the target gas optical absorption with minimum interference from other gases. The off-line wavelength is selected near the wing of the target gas optical absorption, with minimum interference from other gases and high ground surface reflectivity. In the present invention, the on line and off-line wavelengths are selected to be 3369.8, 3389 and 3429 nanometers for ethane, methane and the background, respectively. Note that these specific wavelengths have not been used in the prior art and as it was mentioned earlier, the criteria for the on-line wavelength-selection is that the absorption is expected to be only dominated by methane and ethane, and for the off-line wavelength, the absorption is expected not to be dominated by methane, ethane or by atmospheric particles.

Another aspect of the present invention uses stable continuously tunable lasers. Therefore, three ND:YLF continuously tunable lasers were designed and implemented for methane and ethane trace gases and background, respectively. The present invention also measures the target gases' concentration path-lengths. Therefore, the 3-line tunable DIAL laser system, according to the present invention, measures the concentration path-lengths for the two selected target gases for each scanned spot. The present invention employs a statistical analysis of the multiple concentration path-length measurements for the two target gases along the flight path. Finally, the present invention displays, stores and communicates the position, size, and shape of the gas plumes associated with pipeline leaks.

The present invention, as schematically shown in FIG. 1, comprises an aircraft 110, an on board 3-line tunable differential absorption lidar (DIAL) laser Fluid Pipeline Leaks Detection System 120, a transmitted laser beam 130, trace gases 150, a buried pipeline 160, a leak area 170, a ground surface type 180, a 3-dimensional section of the ground with the pipeline, a leak area and the trace gases 190, an aircraft flight altitude 140 (~500 m), and a cleared pipeline access area 105. Based on an optimally previously determined flight path, the aircraft 110 flies toward buried pipeline 160, in order to detect leak area 170, comprising natural gas or oil pipeline leaks. During the flight an on board GPS and Inertial Measurement Unit (IMU) positional system (not shown herein) guide the pilot toward a target location that emanates trace gases 150. When the aircraft reaches the target location, the laser beams 130 are automatically pointed to the target as the scanner system scans the surrounding central target regions. Then a returned light is analyzed to develop two-dimensional gas-maps or images of both methane and ethane plumes in units of concentration path-length.

In a DIAL measurement system two, essentially single-wavelength, laser pulses are transmitted. One laser pulse of a specific wavelength is chosen which is absorbed by the gas of interest, the other laser pulse at a different wavelength is not absorbed. The energy reflected back to the sensor for both wavelengths is measured and combined to generate an estimate of the target gas' concentration length. This section describes this process in more detail.

The energy which is reflected back to the sensor is described by the following relationship, $$E \propto \frac{E_T \rho_\pi \exp[-2(CL_p + C_{bg}R)\sigma(\lambda)]}{R^2}, \quad (1)$$

where $E_T$ is the transmitted energy, $\rho_\pi$ is the surface reflectance, $CL_p$ is the concentration-length product of the plume, $C_{bg}$ is the background concentration of the gas, R is the range to the surface, and $\sigma(\lambda)$ is the absorption cross-section of the gas as a function of wavelength. In this work, it will be assumed that $E_T$ is constant from pulse-to-pulse (since any changes can be measured and accounted for), that $\rho_\pi$ is 0.005 and does not depend upon wavelength for the small range of wavelengths considered, that R is nominally 500 m, and that the cross-section $\sigma(\lambda)$ does not change significantly due to pressure and temperature changes along the path. This last assumption would not be true for paths which change by many kilometers in altitude, but is reasonable for a 500 meter aircraft altitude. Also, we note that it might be necessary to re-measure $\sigma(\lambda)$ when the system operates in regions where ground level is much higher than sea level.

The term which is wavelength dependent in Equation (1) is the cross-section, $\sigma(\lambda)$. Many of the terms which do not change can be canceled by measuring at two wavelengths and dividing the results. Let $E_1$ denote the energy measurement at one wavelength, and $E_2$ denote the measurement at a second wavelength. Then $$\frac{E_1}{E_2} = \frac{\exp[-2(CL_p + C_{bg}R)\sigma(\lambda_1)]}{\exp[-2(CL_p + C_{bg}R)\sigma(\lambda_2)]}. \quad (2)$$

Taking the natural logarithm of the above, $$\frac{1}{2}\log\left(\frac{E_1}{E_2}\right) = (CL_p + C_{bg}R)(\sigma(\lambda_2) - \sigma(\lambda_1)). \quad (3)$$

The cross-section can be measured offline or in real time (using a gas cell onboard the aircraft). In either case, the cross-section at each wavelength is a known value, therefore $$\frac{1}{2(\sigma(\lambda_2) - \sigma(\lambda_1))}\log\left(\frac{E_1}{E_2}\right) = (CL_p + C_{bg}R). \quad (4)$$

Equation 4 is the measurement process modeled in this work. However, there are additional processing possibilities, since R can also be measured by the system and $C_{bg}$ can be estimated or measured. It would then be possible to produce an estimate of $CL_p$. In the final system, it is likely that an estimate of $CL_p$ alone will be an important part of the product, but analysis of Equation 4 is sufficient to characterize plume detection performance.

In equation (4) the effect of differences in atmospheric concentration length ($C_k$) has not been considered. But equation (5) includes the effect of differences in atmospheric concentration length, where Ck can be estimated or measured.

$$\frac{1}{2(\sigma(\lambda_2) - \sigma(\lambda_1))}\log\left[\left(\frac{E_1}{E_2}\right) - 2C_k\right] = (CL_p + C_{bg}R) \quad (5)$$

Figure 2:
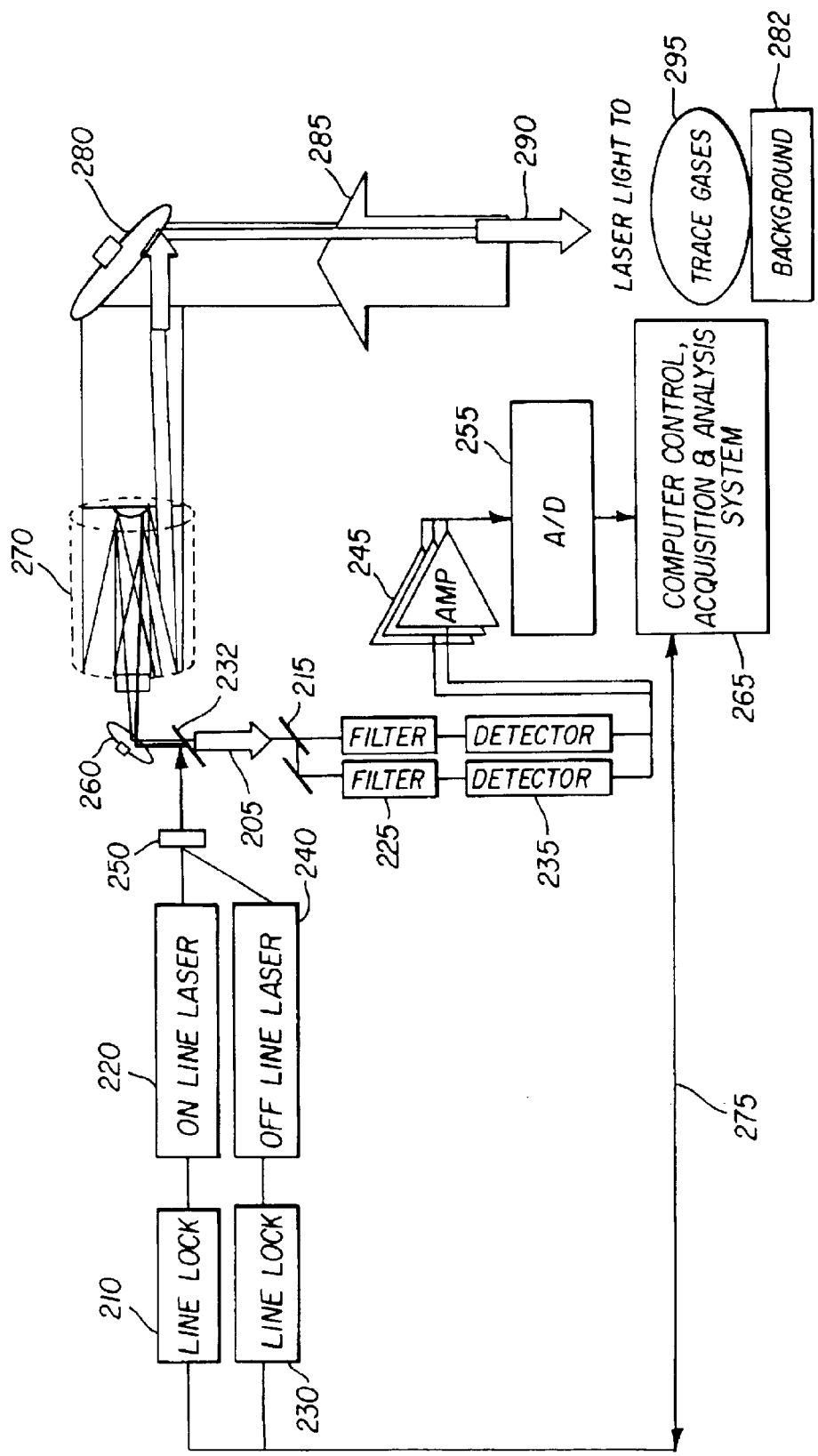
FIG. 2 is a block diagram of a prior art DIAL, gas detection system.

In order to appreciate the present invention, a system block diagram of a prior art DIAL system is shown in FIG. 2. Single on-line laser 220 and one off-line laser 240 are locked by electronic control signals 275 onto two different wavelengths by line lock amplifiers 210 and 230, the on-line wavelength is selected close to the peak of a target gas' optical absorption and the off-line wavelength is selected near the wing of the target gas' optical absorption wavelength. The on-line and off-line laser beams 220 and 240, respectively, are combined by Holographic Grating 250 and transmitted by a fast scan mirror 260 trough a telescope 270 and directed and guided by the slow scan mirror 280. Finally, for the region of interest, trace gases in the atmosphere near the ground are sequentially scanned by laser beams 290. Then, the laser beam 290 is scattered and transmitted by a trace gas 295, reflected by the background 282 scattered and transmitted again by to trace gas 295. Next, the returned light 285 is reflected by the slow scan mirror 280 into a telescope 270 and is separated by beam splitter 232 from the transmitted laser beam 205 to another set of beam splitters 215, then passes through a set of filters 225 to only pass the on-line and off-line wavelengths, then onto a set of detectors 235 to optimally convert the returned light to an electronic signal. Then the signal is electrically amplified by an amplifier 245 and converted to a digital signal by a set of A/D converters 255. The digitized signal is processed and analyzed by the computer 265 to compute the ratio between the on-line and off-line returned signals, which is directly proportional to the target gas concentration path-length.

Figure 3:
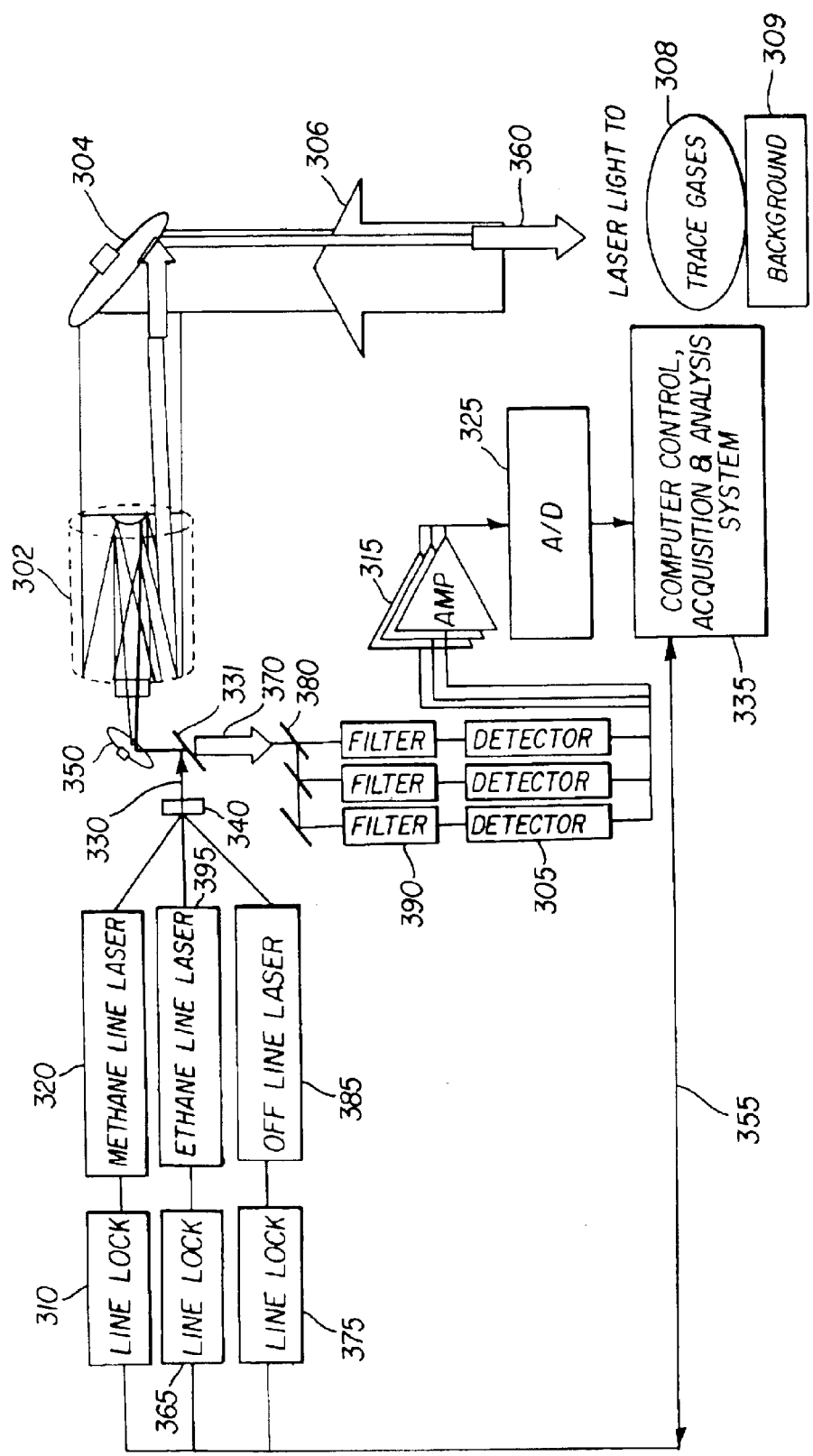
FIG. 3 is a block diagram of a 3-line tunable DIAL laser fluid pipeline leak detection system according to the present invention.

In the prior art, only one trace target gas' signature characteristic is selected and measured. In contrast, in the present invention more than one trace target gas' signature characteristic is used to improve the robustness, sensitivity and performance capability of the gas and oil pipeline leak detection system. A simplified system block diagram of the present invention, the 3-line tunable DIAL laser optical sensor system, is shown in FIG. 3. One on-line laser for methane 320, one on-line laser for ethane 395 and one off-line laser 385 are locked by electronic control signals 355 onto three different wavelengths by line lock amplifiers 310, 365 and 375, respectively-, the on-line wavelengths are selected close to the peak of a target gas' optical absorption characteristics and the off-line wavelength is selected near the wing of the target gas' optical absorption wavelength. The two on-line and one off-line laser beams 320, 395, and 385, respectively, are combined by holographic grating 340 to form combined laser beam 330. The combined laser beam 330 is transmitted by a fast scan mirror 350 trough a telescope 302 and directed and guided by a slow scan mirror 304 to form laser beam 360. For the region of interest, trace gases in the atmosphere near the ground are sequentially scanned by laser beam 360. Laser beam 360 is scattered and transmitted by trace gas 308, reflected by background 309, scattered and transmitted again by trace gas 308, becoming returned light 306. The returned light 306, from the transmitted laser beam 360, is reflected by the slow scan mirror 304 into the telescope 302, and separated by a beam splitter 331 to form a return light 370. Returned light 370 passes through a set of beam splitters 380 before encountering a set of filters 390. Filters 390 only pass the two on-line and one off-line wavelengths, before a set of detectors 305 optimally converts the returned light to an electronic signal. The electronic signal is electrically amplified by an amplifier 315, converted to a digital signal by a set of A/D converters 325. The digitized signal is processed and analyzed by a computer 335 to compute the ratio between the two on-line and off-line returned signals, which are directly proportional to the target gases concentration path-lengths.

Multiple sources of a selected target gas, for example methane, and variability of the ground surface's reflectivity type increase the probability of a false alarm. Hence, the 3-line tunable laser DIAL system implemented by the present invention minimizes false alarms from detecting multiple sources of target gas and variable ground surface reflectivity.

Figure 4:
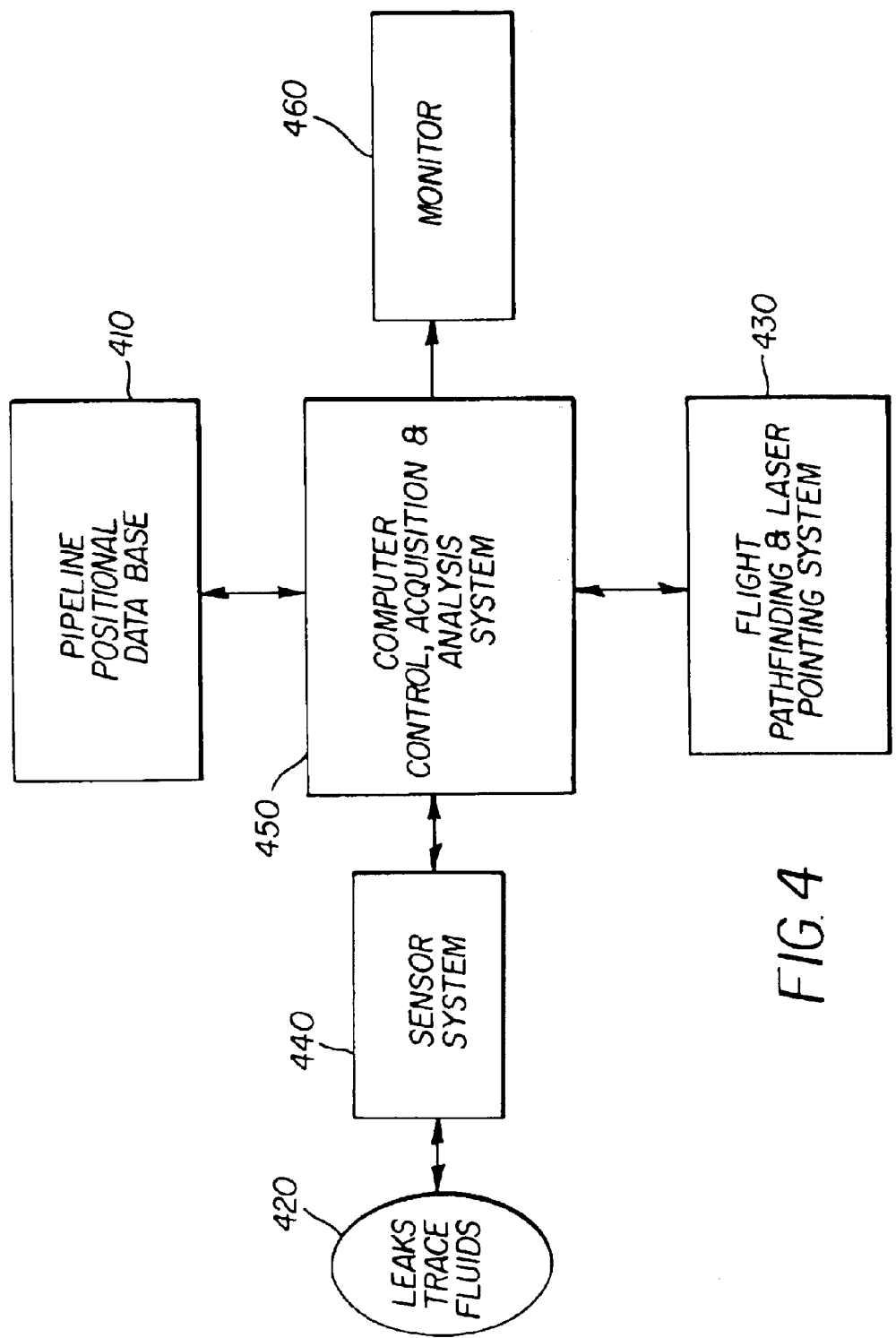
FIG. 4 is an exemplary high-level block diagram of the 3-line tunable DIAL laser fluid pipeline leak detection system according to the present invention.

An exemplary block diagram of the system is shown in FIG. 4. Consumer-acquired pipeline positional data is first processed, filtered, normalized, and stored in pipeline positional database 410. Normalizing the consumer-acquired pipeline positional data entails applying one standard file format to the consumer-acquired pipeline positional data. The normalized positional data for a region of interest is downloaded into a computer control, acquisition and analysis system 450. A flight path-finding and laser pointing system 430, in communication with the computer control, acquisition and analysis system 450 guides an aircraft along a predetermined flight path and points the laser beams at a predetermined point. As part of the flight path-finding and laser pointing system 430, on-board aircraft positional and motion measurement instruments take corrective action to guide the aircraft and the laser to other points along the flight path. A sensor system 440, also in communication with the computer control, acquisition and analysis system 450, transmits laser beams to leaking trace fluids 420 and also receives returned light from the leaking trace fluids 420. The computer control, acquisition and analysis system 450 sends control signals to the sensor system 440 and receives signals from the sensor system 440 to monitor, store and analyze leak concentrations.

Figure 5:
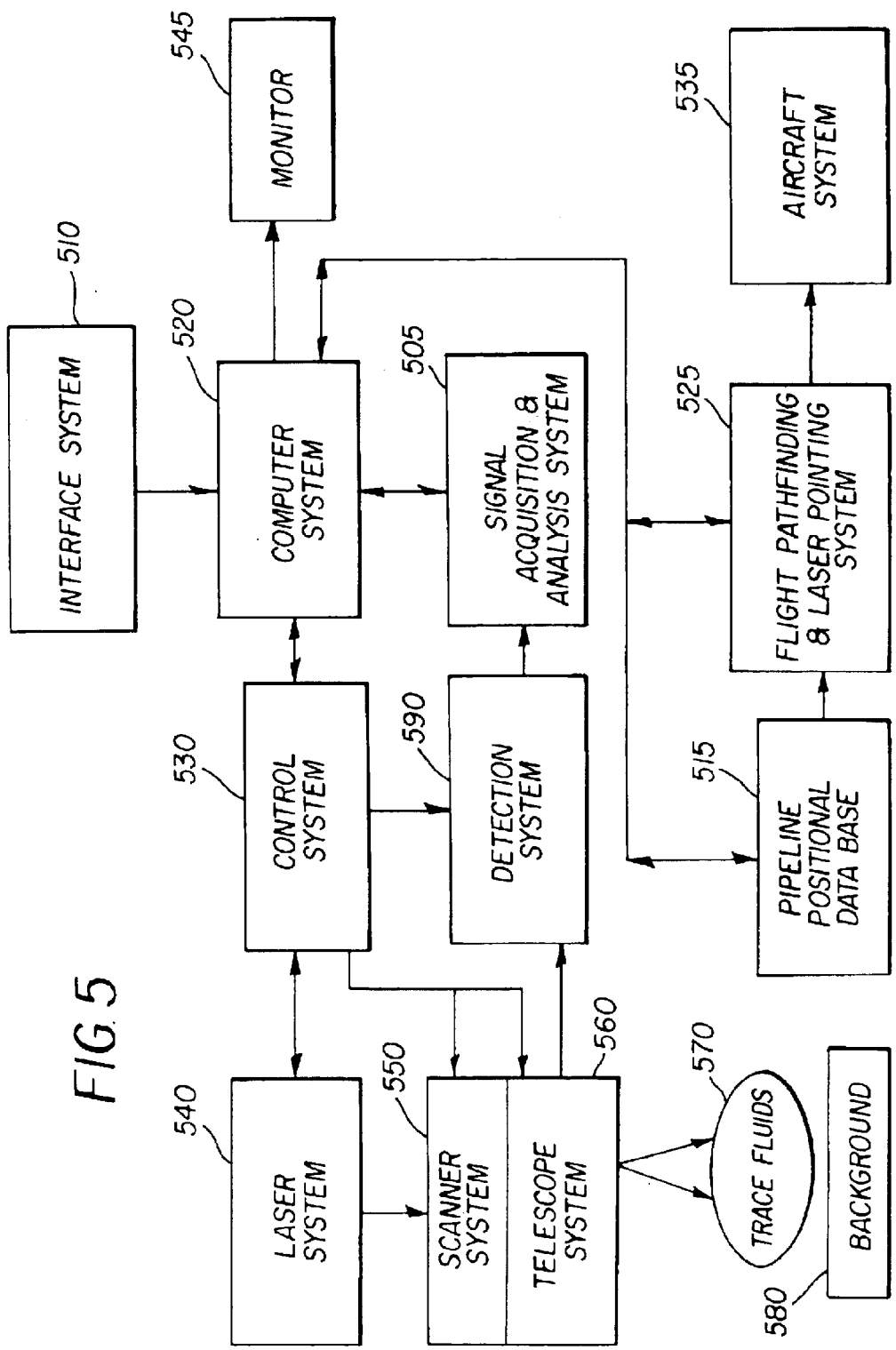
FIG. 5 is a mid-level block diagram of the 3-line tunable DIAL laser fluid pipeline leak detection system according to the present invention.

A more detailed block diagram of the present invention and its primary sub-system 500 is shown in FIG. 5. The primary subsystem 500 includes an Interface System 510 with Graphical User Interface (GUI) software for starting, stopping, setting-up, monitoring and controlling of the operations of the primary subsystem 500. A Computer System 520 has a high end powerful processor (e.g. an Intel Pentium™ chip or an AMD Athlon™, or an IBM PowerPC 750CX), and various hardware components, such as a signal processor and analog to digital (A/D) converters, along with one or more interfaces for communicating with other components of the primary subsystem 500. For example, there are links to a scanner 550, a control system 530, a signal acquisition and analysis system 505, and a flight path-finding and laser pointing system 525 with a Global Positioning System (GPS). The entire primary subsystem has removable hardware drives and various monitors to display process conditions.

The Signal Acquisition and Analysis System 505 has a signal process board for signal processing and acquisition and analysis software to measure, record and display measured concentration levels of ethane and methane.

The primary subsystem 500 includes an aircraft system 535. The aircraft system 535 may be a Cessna™ 402B aircraft or other aircraft capable of flying at ~500 meter altitude with speed of ~67 meter per second, carrying a 3-line tunable DIAL laser fluid pipeline leaks detection system and the on board flight path-finding and laser pointing system 525.

Specifically, the flight path-finding and laser Pointing System 525 includes a portable global positioning system (GPS) and an Inertial Measurement Unit (IMU) and links to the computer system 520 to continuously update the position of the aircraft and direct the laser beams, utilizing laser system 540 via the control system 530, in accordance with the current position of the aircraft.

A Pipeline Positional Database 515 includes software algorithms to process, filter and normalize a consumer acquired pipeline positional data set and an on board GPS and IMU real-time positional data to predict an optimal flight path and update the pipeline positional data base with the predicted optimal path map.

Control System 530 includes all electronic and temperature control circuits for operating the 3-line tunable laser system 540. For example, precise control feedback loops for the current requirement for each laser diode, temperature sensors, laser cavity tuners that lock each the Nd:YLF; laser outputs to its respective seed laser source, timing circuits that generate timing pulses for timing of each laser activation, along with timing of the Q-switching in the laser system 540 and timing for the signal acquisition and analysis system 505. Accordingly, the laser system 540 includes implementation of a 3-line, direct detection, DIAL laser transmitter system.

A Laser system 540 operates in the mid-wave infrared spectral region and employs three all solid-state Nd:YLF laser transmitters. These lasers will output single frequency light and operate at pulse repetition rates of 3050 Hz. Each laser will produce about 0.68 W of output power. The lasers are tunable and locked to the desired wavelengths. The laser system 540 also provides 10 nanoseconds of short single frequency pulses at three different wavelengths.

A Scanner System 550 includes fast scan rotating wedges and slow scan pitch & roll compensator wedges subsystems. The fast scan rotating wedges are responsible for directing the transmitted laser light coming from the transmitter laser system 540 to the target area. The backscattered light from the target area is also directed into the detection (receiver) system 590 by the scanner system 550. Scanner system 550 also generates a circular rotating illumination pattern around the optical centerline of the transmitter/receiver subsystems. The slow scanning subsystem pitch & roll compensator of the scanner system 550 directs the center of the circular illumination path to the target area.

Telescope System 560 is an optical system that is also called the receiver telescope. The primary function of telescope system 560 is to collect the backscatter light from the target and focus it to the detection system 590. Telescope system 560 is focused at the target area and the portion of the backscatter light that falls on the receiver telescope primary mirror is focused into a collimated beam by the telescope secondary mirror and the collimating lens. A high optical transmission interface filter, with an optical bandwidth that encompasses the three wavelengths, serves to reject wide band background light from the reflected solar radiation, and hot-surfaces thermal emissions.

A Detection System 590 comprises the components and subsystems needed to detect and electronically condition the returned signal at three mid-IR wavelengths. The detection system 590 may also be termed the receiver system. The detection system 590 employs direct detection of signal power and uses three separate detectors, where each detector, views different percentages of the returned beam, to achieve a large dynamic range due to both ground (background) reflectivity variations and the attenuation from the absorbing trace gases. Subsequently, the detected electronic signals are amplified and digitized.

The primary subsystem 500 is designed to detect trace fluids 570. For gas and pipeline leaks, trace fluids 570 are methane and ethane. One objective is selection of characteristics associated with trace fluids 570, as fluid pipeline leaks, that will enable one to reliably and robustly detect possible pipeline leaks.

Detection of trace fluids 570 may be affected by background 580. Background 580 is defined as reflection from the ground surface. Background 580 may be bushes, soil, water, trees, sand and so on. The background 580 reflects the backscattered light to telescope system 560.

A monitor 545 is included in primary subsystem 500 to display various Graphical User Interfaces (GUIs) that enable monitoring and analysis of relevant process conditions for the 3-line DIAL laser fluid pipeline detection system. The computer system 520 sends the control signals to the control system 530 and receives information monitoring signal information from the control system 530. The computer system 520 also accesses the prior optimally determined flight path data base interface 510 and the on board GPS and IMU positional path-finding and laser pointing subsystem 525 to point the laser beams, while controlled by the control system 530 and determines the next target location which is in turn passed to the aircraft system 535. The control system 530 sends an electronic locking signal to the laser system 540 and also controls the temperature of the all the diode lasers in laser system 540. The laser system 540 generates three nearly simultaneous at pulse laser beams (no more than 10 nanoseconds a part) at the specified wavelength for transmission to the target location. The transmitted laser beams pass through the scanner system 530, the atmosphere, the trace fluids 570; and finally strike the background 580. The returned signal from the background 580 passes again through the trace fluids 570 and the atmosphere, back to the telescope system 560. The returned light enters the aperture of telescope system 560 and is focused on the detectors in detection system 590. The detected analog signal is optimally digitized for the optimal dynamic range by the detection system 590 and the digitized signal will be analyzed by the signal acquisition and analysis system 505 to estimate the trace fluid's target concentration path length. The software algorithm in computer system 520 statistically analyzes the estimated concentration path length. Finally the analyzed signals are stored in the computer system hard disk and the monitor 540 displays two-dimensional or three-dimensional gas-maps.

Figure 6:
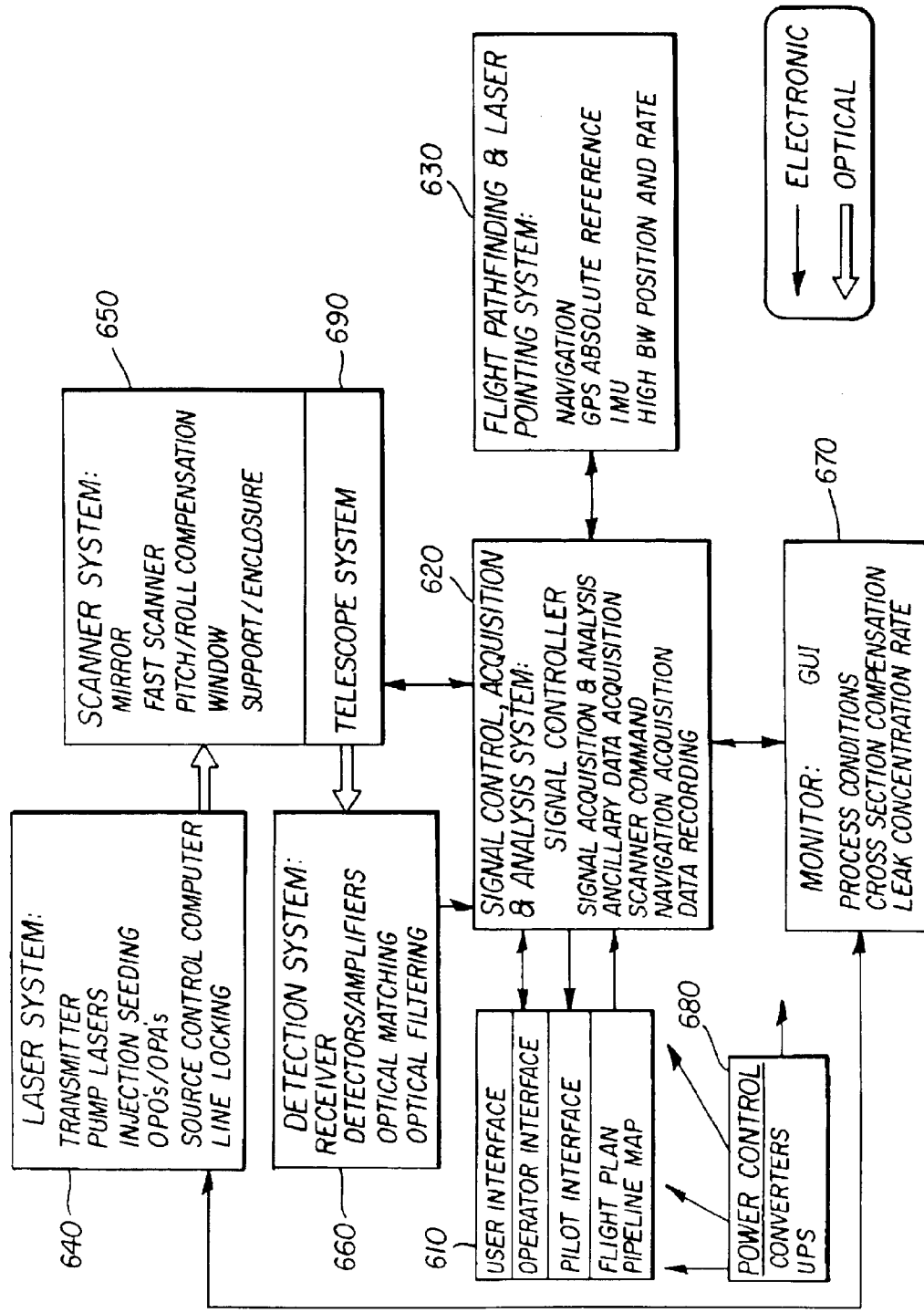
FIG. 6 is a mid-level block diagram of the 3-line tunable DIAL laser fluid pipeline leak detection system, according to the present invention, with the list of components for each primary subsystem.

The components of each primary subsystem, as shown in FIG. 5, for generating source #1 laser of the present invention are described further in FIG. 6. The components described herein whether individually and/or grouped are not solely exclusive. Equivalent components may be substituted and are anticipated.

Referring to FIG. 6, a laser system 640 may include a transmitter, pump lasers, Optical Parametric Oscillator (OPO), Optical parametric Amplifier (OPA), injection seeding, a computerized laser source controller and a line locking mechanism. The components of the scanner system 650 may include a mirror, fast scan wedges, slow scan pitch/roll compensation wedges, and a window support/enclosure.

Detection system 640 may include an optical filter, optical matching, detectors, amplifiers and analog to digital convectors. Whereas, the flight path-finding and laser pointing system 630 may include navigational components such as a global positioning system (GPS), an Inertial Measurement System (IMU) and high bandwidth aircraft position and altitude updating equipment.

The signal control, acquisition and analysis system 620 may include components that enable signal control, signal acquisition, signal analysis, ancillary data acquisition, command of the scanner, acquisition of navigational data and data recording. User interface system 610 may have components for user interfacing, pilot interfacing, and a flight plan that incorporates a target pipeline map. A monitor 670 displays a GUI, process conditions and concentration leak rates. Power controller 680 provides electric power to all the sub-systems.

The signal control, acquisition and analysis system 620 (comprising 520, 530 and 505 as shown in FIG. 5.) sends the control electronic locking signals to the laser system 640 and receives monitoring signal information from the laser system 640. The signal control, acquisition and analysis system 620 also accesses the previously determined optimal flight path data from flight path database interface 610; and controls the on board GPS and IMU positional path-finding and laser pointing subsystem 630 to point the laser beams through the scanner system 650. Additionally, the signal control, acquisition and analysis system 620 determines the next target location and passes the target information to the aircraft system 535 (shown in FIG. 5). The signal control, acquisition and analysis system 620 also controls the temperature of the all the diode lasers in the laser system. The laser system 640 generates three nearly simultaneous pulse laser beams (e.g., within 10 nanoseconds a part) at a specific wavelength and transmits the pulse laser beams to the target location through the scanner system 650. The transmitted laser beams pass through the atmosphere, through the trace fluids, and finally strike the background. The returned signal from the background passes once again through the trace fluids and the atmosphere as it returns to the telescope 690. The returned light enters the aperture of telescope 690 and is focused on the detectors in the detection system 660. The detected analog signal is digitized for the optimal dynamic range used by the detection system 660 and the resulting digitized signal is analyzed by the signal control, acquisition and analysis system 620 to estimate the trace fluid's target concentration path length. The software algorithm statistically analyzes the estimated concentration path length in the signal control, acquisition and analysis system 620. Finally the analyzed signals are stored in a hard disk of the signal control, acquisition and analysis system 620 and the monitor 670 displays two-dimensional or three-dimensional gas maps.

Figure 7:
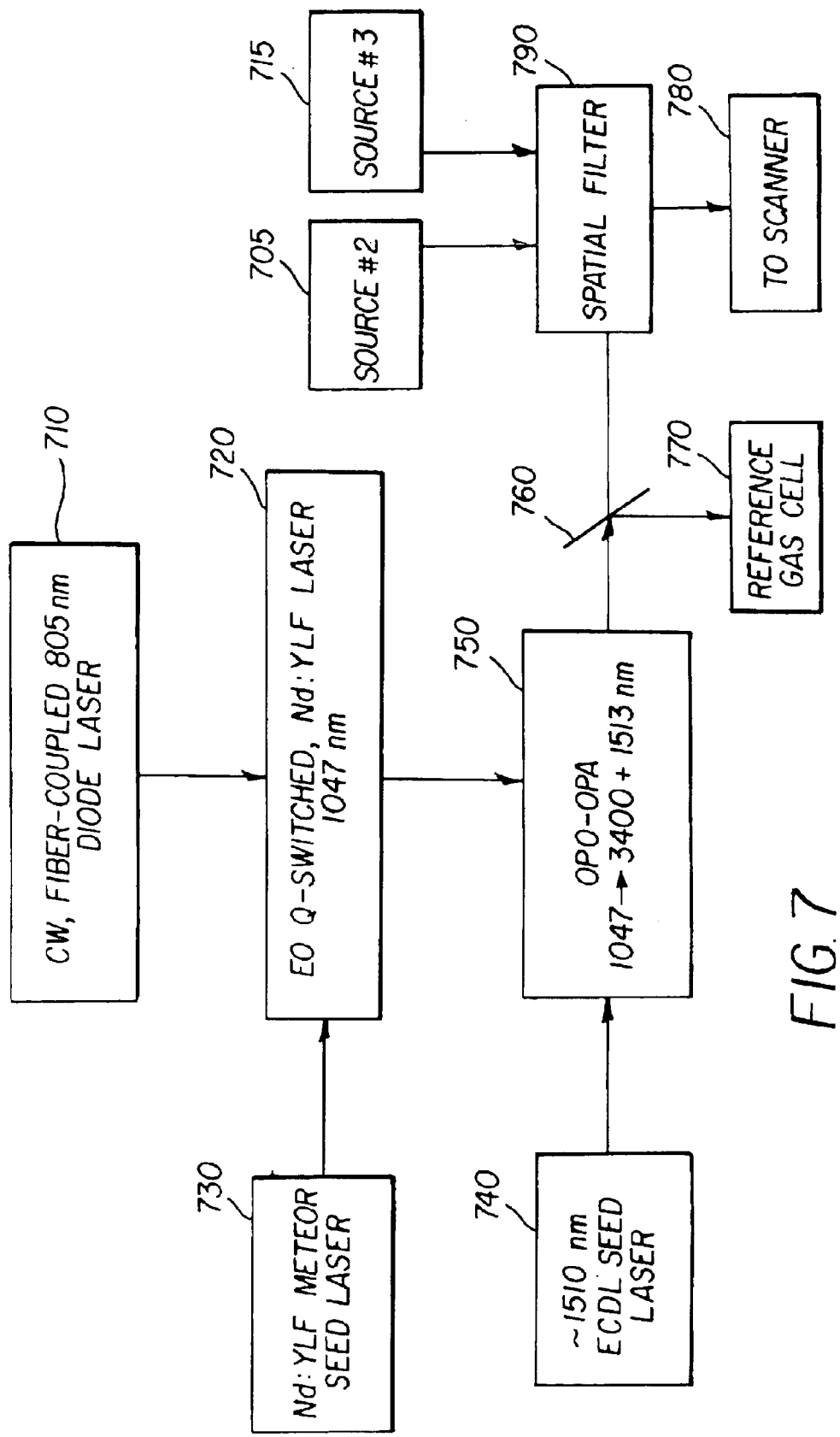
FIG. 7 is a block diagram of a 1-micrometer optical parametric oscillator and amplifier for generating a selected wavelength.

FIG. 7 shows the simplified block diagram of the laser source's transmitter, which employs a 1 $\mu$m Nd:YLF laser that pumps an optical parametric oscillator (OPO)—optical parametric amplifier (OPA) frequency converter. The OPO is seeded to ensure single-frequency operation. As shown in FIG. 7, # 2 laser source (705) and # 3 laser source (715) are generated and combined by the spatial filter 790 into a single transmitted beam.

Different laser source selection approaches were considered based on the source efficiency, $\eta$, is the electrical-to-optical efficiency of the approach not including seed laser power and cooling power.

The short pulse width and precise timing of the pulses dictates the use of actively Q-switched lasers. Q-switching is advantageous for short pulses and active control is advantageous for precise timing. The laser source must be compact and efficient to be compatible with what is likely limited aircraft space and power. There are no commercially available sources that meet these requirements. Conventional laser technology generally uses nonlinear optical techniques for shifting the wavelength of well-developed lasers in the short-wave-infrared (SWIR) or long-wave infrared (LWIR) to access mid-wave infrared (MWIR) wavelengths, such as the wavelengths employed in the present invention. Examples of SWIR and LWIR lasers that can be frequency-shifted to the MWIR are neodymium (Nd) solid-state lasers and carbon dioxide (CO2) gas lasers, respectively.

Referring to FIG. 7, a 1 $\mu$m DPSSL/OPO-OPA laser source single tunable frequency technique is used to generate the selected wavelengths. OPO-OPA 750 is pumped by a Q-switched Nd:YLF laser 720 operating at 1047 nm. The Nd:YLF laser is pumped by a fiber-coupled diode laser 710 operating at 805 nm and that is also injection seeded by CW (continuous wave), single frequency 1047 nm light from a common seed source. The OPO-OPA 750 is injection seeded by external-cavity diode laser operating at ~1510 to assure single frequency output at 3400 nm. The combination of Nd:YLF seed laser 730, ECDL seed laser 740, 1 $\mu$m DPSSL 710, OPO—optical parametric amplifier (OPA) 750 subsystems, shown in FIG. 7, increases the wavelength conversion efficiency by using two nonlinear processes in the OPO cavity. An OPA is used to convert some of the unneeded power produced by the OPO crystal into 3400 nm output. As shown in FIG. 7, the OPO process converts the Nd:YLF pump wavelength (1047 nm>3400 nm+1510 nm) and the OPA process then produces more 3400 nm output (1510 nm>3400 nm+2720 nm). This means that a single pump photon can produce two 3400 nm photons. More MWIR photons are produced than incident pump photons as a result of greater than 100% photon conversion efficiency. Therefore, the two-step conversion leads to a higher overall optical-to-optical conversion efficiency, ~25% or greater. Thus, the overall system efficiency with this particular approach is ~2.

Figure 8:
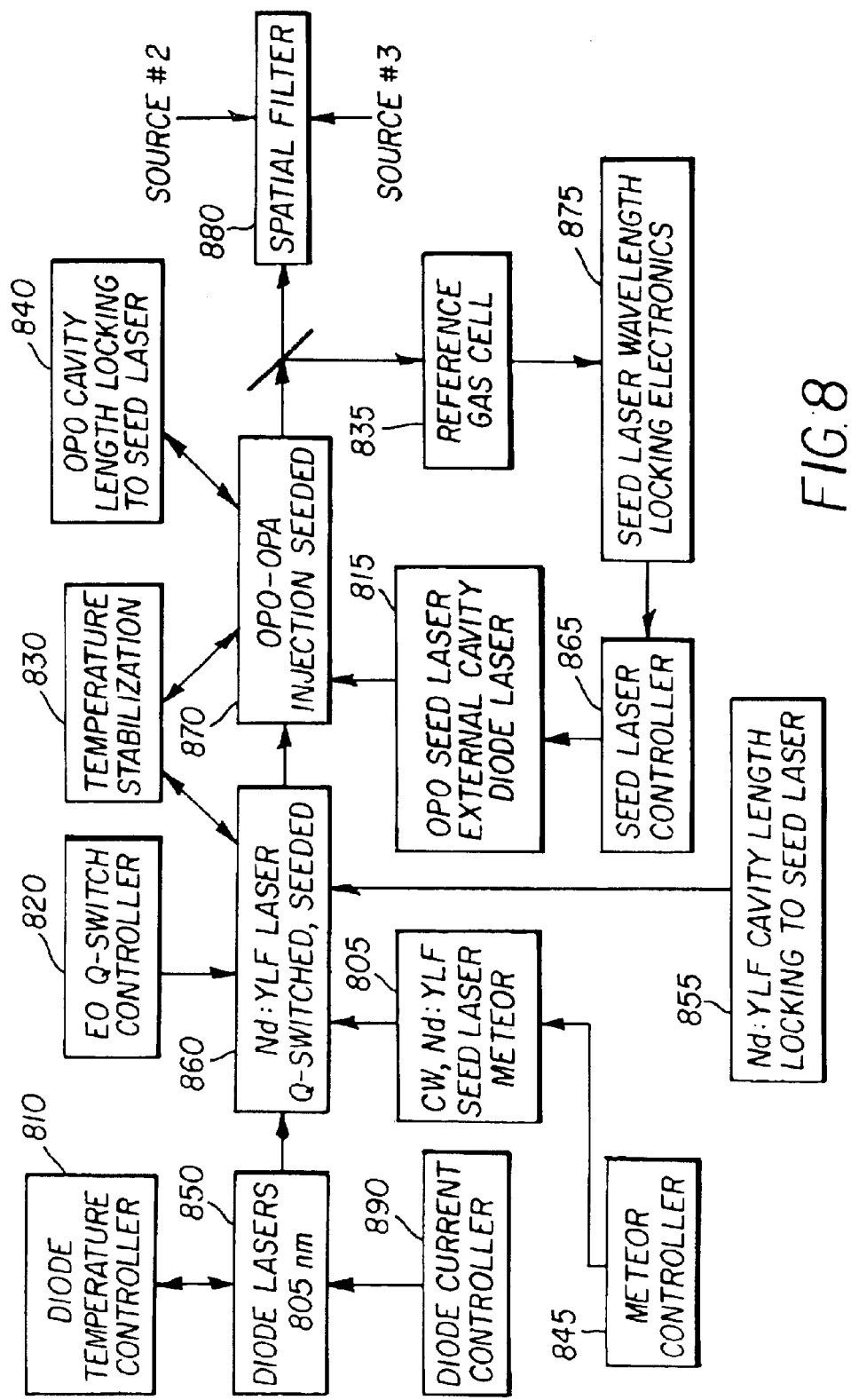
FIG. 8 is a block diagram of a 1-micrometer optical parametric oscillator and amplifier for generating one of the selected 3-line wavelength.

A block diagram of a single laser source, in greater detail, is shown in FIG. 8. The output of an 805 nm pump diode laser 850 passes through an optical fiber is collimated and focused into a Nd:YLF rod 860 to provide gain for the laser. Also the Nd:YLF laser 860 is Q-switched and seeded by the 1047 nm meteor seed laser 805. The 1047 nm output of 860 is injected into the OPO-OPA laser cavity 870 through a thin-film polarizer. Also the OPO-OPA laser cavity 870 is seeded by the 1510 nm ECDL seed laser 815. The OPO-OPA is a 4-mirror ring cavity containing 2 PPLN (periodically-poled lithium niobate crystals). The first crystal is chosen to produce 3400 nm and 1510 nm light with 1047 nm pump, while the second crystal (should be a different #) is chosen to produce 3400 nm and 2700 nm light with 1510 mm pump. A cavity 870 resonates at 1510 nm and is injection seeded at this wavelength through the output coupler. The cavity length is locked to the seed frequency by 840 by using the Pound-Drever-Hall (PDH) technique with Radio frequency modulation applied to the diode laser seed 1510 run. Diode subsystems 810 and 890 controls temperature and current of the pump diode laser 850, respectively. Subsystem 820 controls the Q-switching and seeding of the cavity via operation 860. Meteor controller 845 controls the 1047 $\mu$nm wavelength of seed laser 805. The 855 subsystem locks the cavity length of seed laser 860. A seed laser controller 865 controls the 1510 nm seed laser wavelength; and seed laser wavelength electronics 875 locks the seed laser at a desired wavelength.

Figure 9:
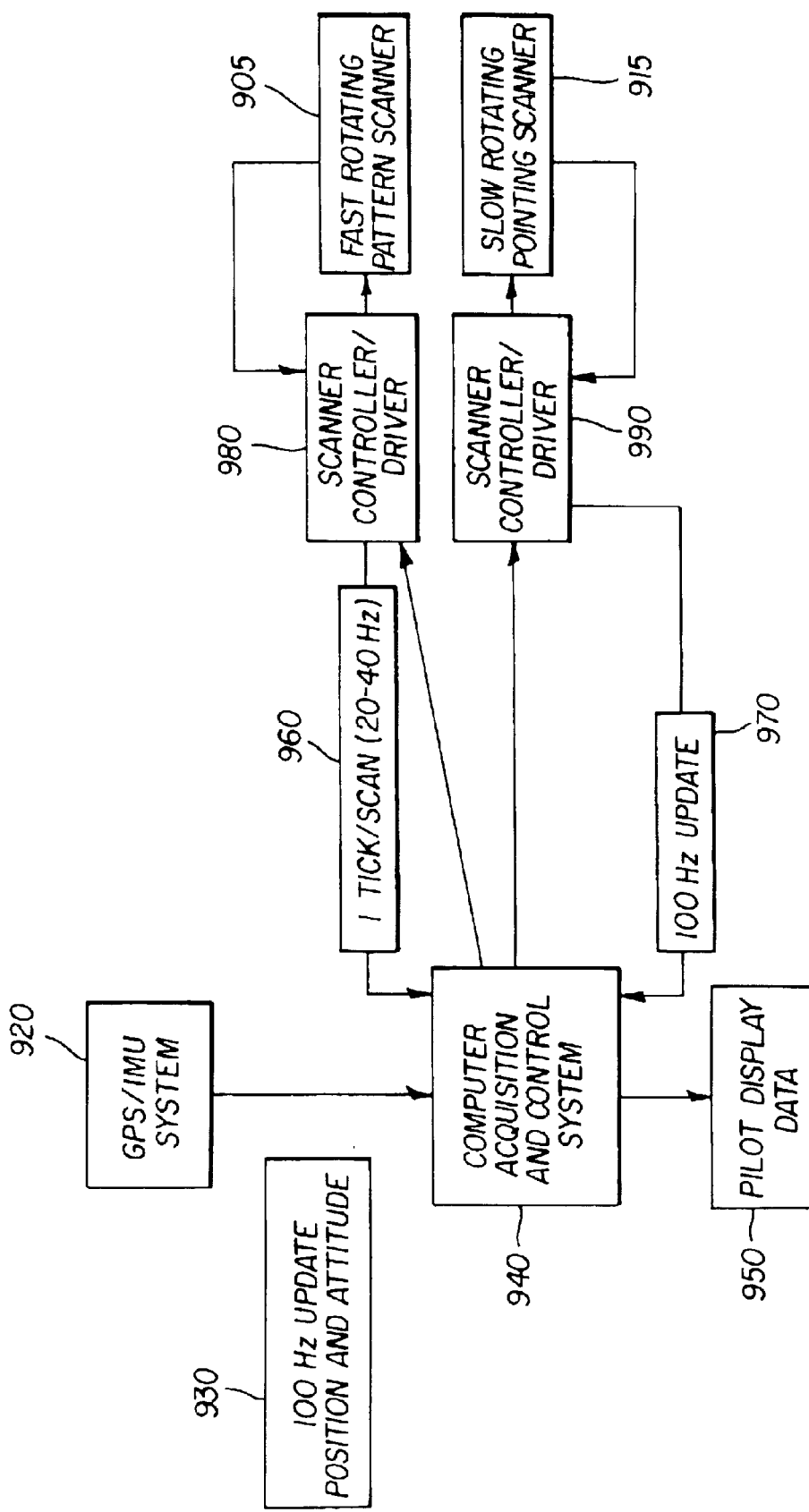
FIG. 9 is a block diagram of the flight path-finding system according to the present invention.

A block diagram of a flight path-finding and laser pointing subsystem is shown in FIG. 9. As mentioned earlier, the present invention measures the trace signature gases of the fluid pipeline leaks concentration level within a predefined corridor, along a pipeline path. To perform this task, the laser pointing subsystem actively and continuously directs the three combined beams according to the current position of the aircraft and the desired measurement position on the ground. A fast rotating circular scanner 905 and a slow rotating pointing scanner 915 directs the three beams in a constant and circular pattern according to the current aircraft position and desired corridor coverage. An ideal flight plan path will be generated for optimal ground coverage along the flight plan. A GPS and/or IMU system 920 is queried at 100 HZ via an update position and altitude module 930 to determine the current aircraft position and altitude. Based on the current position, the nearest point on the ideal flight plan will be determined along with its associated ground position. The circular pattern is pointed at this ground position with reference to the current altitude. The current positional information is used by a computer acquisition and control system 940 to communicate with a scanner controller/driver 990 for controlling the slow rotating pointing scanner 915 to the target area and display the information to a pilot data display 950. Either or both of the scanner controller/driver 980 and scanner controller/driver 990 control drivers that direct the three-laser beams to the target position on the ground. Scanner controller/driver 980 provides a scan instruction 960 for every 1 tick/scan @ 20–40 Hz to the computer acquisition and control system 940.

Figure 10:
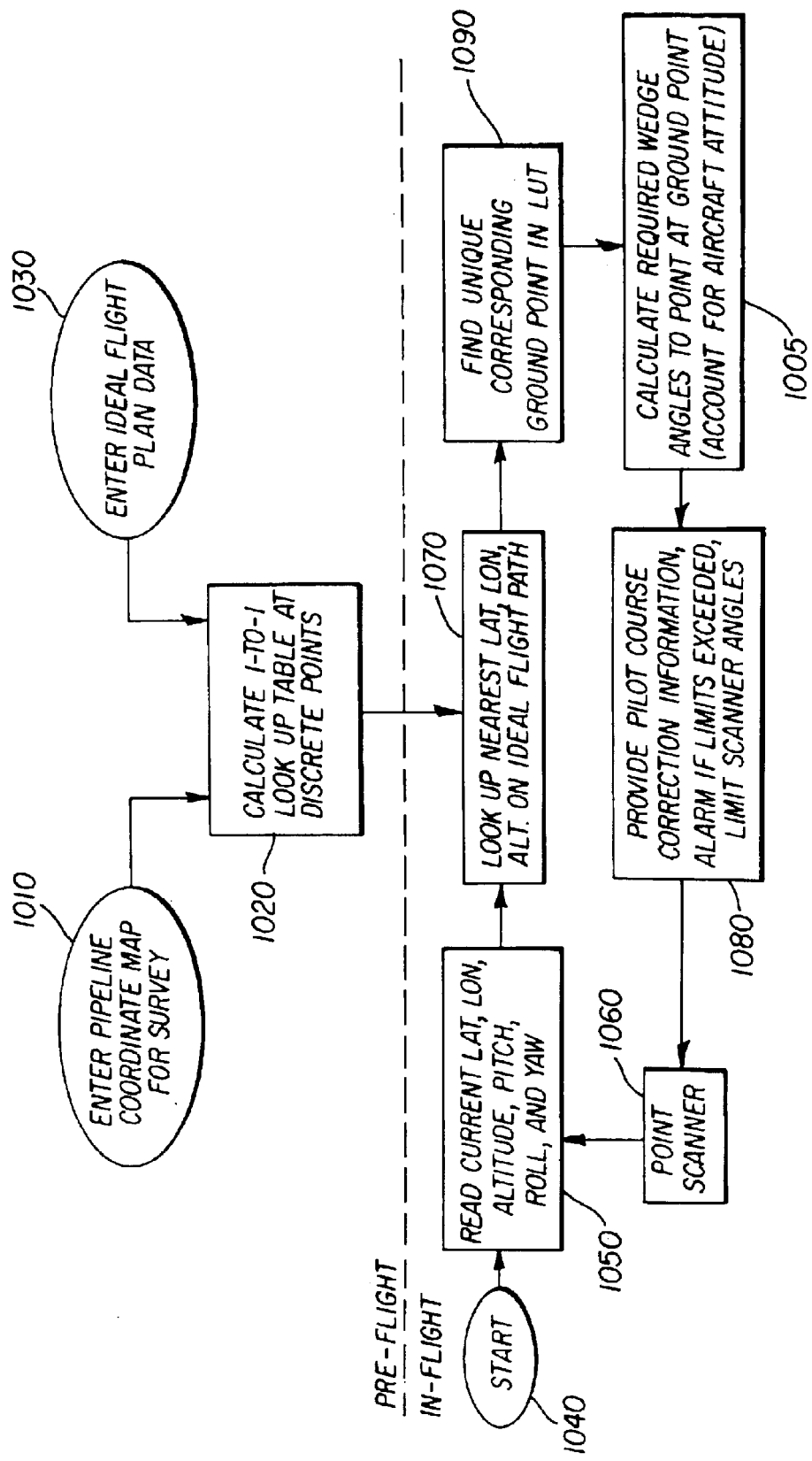
FIG. 10 is a block diagram of the laser pointing system according to the present invention.

The pipeline positional database subsystem software algorithm is shown in FIG. 10. For stable pointing control, a unique pointing position is needed at every moment during the flight. Because the pipeline may travel an irregular path that cannot be closely followed by the aircraft, ambiguities associated with the pointing target are expected. Therefore, initially, a preflight pipeline positional information operation 1010 and an ideal flight path operation 1030 are used to calculate a 1-to-1 look up table in operation 1020. Subsequently, start operation 1040 begins flying the aircraft, at the predetermined altitude, to the target position. The aircraft's current positional data is measured by an on board GPS and IMU in operation 1050, based on the target position. Finding the nearest latitude, longitude, altitude along the ideal flight path occurs in operation 1070. Finding a unique corresponding point on the ground happens subsequently in operation 1090. Whereupon operation 1005, the required wedge angle to point at the ground point is calculated and provided to a pilot course correction information operation 1080, which points a scanner to direct the three beams to the nearest target ground point in operation 1060.

A schematic of the developed 3-line DIAL laser gas pipeline leaks detection system, with a more detail information of the transmitter and receiver (transceiver) subsystem, is shown in FIG. 11. The three laser sources for the off-line and two on-line wavelengths (1110, 1120, 1130, respectively) are first split by the three beam splitters 1140 to monitor their power by a set of power meters 1170, second, the three laser sources are combined by a holographic grating 1155 so that they are collinear. Collinear beams 1112 enter into a beam-combining grating 1114 to provide a fixed finite source aperture. In this way, any drifts that might occur in laser alignment will show up as easily recognized transmitted pulse energy discrepancies, but will not affect gas concentration length measurement calibrations. The multi-wavelength source beam is then introduced into a set of directing optical path mirrors 1116. A reflected custom optic beam enters onto a galvanometer-driven scanning fast mirror 1118 and is transmitted to illuminate the ground via a large aperture slow scanning mirror 1122 that is also used to compensate the scan swath for aircraft roll and off-track flight errors. As the galvanometer-driven scanning fast mirror 1118 swings through a full angle of 25 degrees, the source beam swings through a 50 degree arc on entering a telescope 1108. Telescope 1108 produces a 5 degree full angle scan of the transmitted beam and traces a 35 m wide ground swath scan 1126 of the laser footprint 1132 on the ground (the additional angle width is included to compensate for aircraft crab angle). Light scattered from the receiver footprint 1128, enters the full telescope aperture via a slow track correction mirror. The fast scanning galvanometer-driven mirror 1118 also reflects the received light in the exit pupil. Thus, the galvanometer-driven scanning fast mirror 1118 shifts the central angle field of view (FOV) of the receiver (in other words, equivalent to shifting the receiver footprint 1128 on the ground) synchronously with the optical centerline of the transmitted beam. The received light then passes through the custom beam-splitter 1111, through a narrow band interference filter 1106, and the filtered light 1104 onto the signal detector 1102, onto the amplifier 1190; and the amplified light 1180 is digitized by 1146. In order to monitor the stability of the locked three wavelengths, a percentage laser beam 1150 from the on-line methane laser source 1130 is passed to subsystems 1160. The gas-cell spectral line pass filters 1165 only pass the selected laser lines, then a set of detectors 1185 convert the laser light to analog electronic signals before passing these signals through a set of power meters (energy meters) 1175 to monitor the laser's power. Then the measured laser power passes through a set of low rate A/D coveters 1195 and finally the output of these A/D converters 1195 is read by computer control acquisition & analysis system 1148. A scanner electronic controller subsystem 1144 controls a fast scan mirror 1122 and a slow san mirror 1124. A pipeline positional database 1142, the computer control, acquisition and analysis 1148 and the flight path-finding and laser pointing 1152 subsystems shown in FIG. 11 were described earlier.

The present invention can be tuned to detect a multiple components of hydrocarbon gases by changing the wavelengths of the 3-line DIAL laser sensor incorporated herein.

The invention has been described with reference to one or more embodiments. However, it will be appreciated that a person of ordinary skill in the art can effect variations and modifications without departing from the scope of the invention. The present invention is tuned to detect gas/oil pipeline leaks, however, it will be understood by anyone skilled in the art that the present invention may be tuned for the detection of hazardous or other materials of interest. It will be further understood that the method can be advantageously used for the exploration of oil/gas or other natural resources of interest.

PARTS LIST

| | |
|---|---|
| 105 | Cleared Pipe access |
| 110 | Aircraft |
| 120 | Airborne 3-line tunable DIAL laser fluid pipeline detection system |
| 130 | Transmitted laser beam |
| 140 | Flight altitude |
| 150 | Trace gases |
| 160 | Buried pipeline |
| 170 | Leak area |
| 180 | Ground surface type: background |
| 190 | A 3D section of the ground |
| 205 | A percent of combined laser beam |
| 210 | Line lock amplifier |
| 215 | Beam splitter |
| 220 | On-line laser |

-continued

PARTS LIST

| | |
|---|---|
| 225 | Filter |
| 230 | Line lock amplifier |
| 232 | Beam splitter |
| 235 | Detector |
| 240 | Off-line laser |
| 245 | Amplifier |
| 255 | Analog to Digital converter A/D |
| 250 | Holographic grating |
| 260 | Fast scan mirror |
| 265 | Computer control, acquisition and analysis system |
| 270 | Telescope |
| 275 | Electronic control signals |
| 280 | Slow scan mirror |
| 282 | Ground surface type: Background |
| 285 | Returned light |
| 290 | Transmitted laser light |
| 295 | Trace Gases |
| 370 | A percent of combined laser beam |
| 310 | Line lock amplifier |
| 331 | Beam splitter |
| 390 | Filter |
| 320 | Methane on-line laser |
| 365 | Line lock amplifier |
| 395 | Ethane on-line laser |
| 380 | Beam splitter |
| 305 | Detector |
| 375 | Line lock amplifier |
| 385 | Off-line laser |
| 315 | Amplifier |
| 325 | Analog to Digital converter A/D |
| 340 | Holographic grating |
| 350 | Fast scan mirror |
| 335 | Computer control, acquisition and analysis system |
| 302 | Telescope |
| 355 | Electronic control signals (Laser line lock communications) |
| 304 | Slow scan mirror |
| 309 | Ground surface type: Background |
| 306 | Returned light |
| 360 | Transmitted laser light |
| 308 | Trace Gases |
| 410 | Pipeline positional data base |
| 420 | Leaks trace fluids |
| 430 | Flight pathfinding & laser pointing system |
| 440 | Sensor system |
| 450 | Computer control, acquisition and analysis system |
| 460 | Monitor |
| 510 | Interface system |
| 520 | Computer system |
| 530 | Control system |
| 540 | Laser system |
| 550 | Scanner system |
| 560 | Telescope system |
| 570 | Trace fluids |
| 580 | Background |
| 590 | Detection system |
| 505 | Signal acquisition and analysis system |
| 550 | Pipeline positional database |
| 525 | Flight pathfinding and laser pointing system |
| 535 | Aircraft system |
| 610 | Interface system |
| 620 | Signal control, acquisition and analysis system |
| 630 | Flight pathfinding and laser pointing system |
| 640 | Laser system |
| 650 | Scanner system |
| 660 | Detection system |
| 670 | Monitor |
| 680 | Power control converters |
| 690 | Telescope system |
| 705 | Single laser source #2 |
| 715 | Single laser source #3 |
| 710 | Fiber-coupled diode laser |
| 720 | The diode-pumped Q-switched, Nd: YLF laser |
| 730 | The Nd: YLF seed laser |
| 740 | External cavity diode laser (ECDL) seed laser |
| 750 | The Optical Parametric Oscillator (OPO)-Optical Parametric Amplifier(OPA) |

-continued

PARTS LIST

| | |
|---|---|
| 760 | Beam splitter |
| 770 | Reference gas cell |
| 780 | Telescope |
| 790 | Holographic grating/spatial filer |
| 810 | Diode temperature controller |
| 820 | Electro-optic Q-switch controller |
| 830 | Temperature stabilization |
| 840 | OPO cavity length locking to seed laser |
| 850 | Diode laser 805 nm |
| 860 | Q-switched Seeded Nd: YLF laser |
| 870 | OPO-OPA injection seeded |
| 880 | Spatial filter/beam combiner to combine the 3 produced lasers into a single transmit beam |
| 890 | Diode current controller 805 Meteor Nd: YLF seed laser |
| 815 | OPO seed laser external cavity diode laser |
| 835 | Reference gas cell |
| 845 | Meteor controller |
| 855 | Nd: YLF cavity length locking seed laser |
| 865 | Seed laser controller |
| 920 | GPD/IMU system |
| 930 | Position and altitude update |
| 940 | Computer acquisition and control system |
| 950 | Pilot display data |
| 960 | Fast scanner update signal |
| 970 | Slow scanner update signal |
| 905 | Fast scanner controller drive |
| 915 | Slow scanner controller drive |
| 980 | Fast rotating scanner |
| 990 | Slow rotating scanner |
| 1010 | Pipeline coordinate map from survey |
| 1030 | Idea flight path data |
| 1020 | Look up table (LUT) |
| 1040 | Start the target location and path calculation |
| 1050 | Read current data (latitude, longitude, roll, pitch and altitude) |
| 1060 | Point scanner (pointing laser) |
| 1070 | Nearest point LUT |
| 1080 | Pilot path correction information |
| 1090 | Corresponding ground point coordinate in LUT |
| 1005 | Pointing angle calculation |
| 1150 | A percent of combined laser beam |
| 1110 | 3389 nm off-line laser light source |
| 1120 | 3336.8 nm ethane on-line laser light source |
| 1130 | 3429 nm methane off-line laser light source |
| 1140 | Beam splitter |
| 1155 | Holographic grating |
| 1170 | Power meter |
| 1112 | Single combined laser beams |
| 1114 | Beam expander |
| 1116 | Directing mirror |
| 1118 | Dual-wedge fast conical scanner |
| 1122 | Dual wedge conical pointing scanner |
| 1124 | Reflected light from ground surface (returned light) |
| 1126 | Ground Swath |
| 1128 | Receiver footprint |
| 1132 | Laser footprint |
| 1108 | Dual-Kirkham telescope |
| 1111 | Directing mirror |
| 1106 | Narrow band interference filter |
| 1104 | Filter returned light |
| 1102 | Detector |
| 1190 | Amplifier |
| 1180 | Amplified signal |
| 1146 | A/D |
| 1160 | Transmitted laser energy measurement sub-system |
| 1165 | Reference gas cell |
| 1185 | Detectors |
| 1175 | Transmitted Energy |
| 1195 | Low rate A/D |
| 1142 | Pipeline positional system |
| 1144 | Scanner diver and position encoders |
| 1148 | Computer control, acquisition and analysis system |
| 1152 | Flight pathfinding and laser pointing system |
| 1154 | Laser line lock communications |

What is claimed is:

1. A system for remote quantitative detection of fluid leaks from a natural gas or oil pipeline by use of an airborne platform; comprising:

a) at least one laser light source for nearly simultaneous illuminating essentially a same target area of two or more target fluids and a background, wherein the two or more target fluids are characterized by two or more absorption wavelengths, and wherein the background has a different wavelength than either of the two or more target fluids;

b) means for pointing the illumination source based on a positioning system;

c) means for scanning for the two or more target fluids in a geometric area along a path using the illumination source;

d) means for signal detection such that a quantitative processing of detection of the two or more target fluids is accomplished;

e) means for controlling operation of the system;

f) signal processing means for the remote quantitative detection of the two or more target fluid leaks;

g) means for path planning and path finding for the positioning of the airborne platform; and h) means for communicating presence of the detected leak from the natural gas or oil pipeline.

2. The system claimed in claim 1, wherein the system uses two or more laser light sources.

3. The system claimed in claim 1, wherein the two or more target fluids are gases having absorption characteristics of gases.

4. The system claimed in claim 3, wherein the gases are methane and ethane.

5. The system claimed in claim 4, wherein the at least one laser light source having a wavelength is tuned to the absorption characteristics of methane, ethane, and reflectance characteristics of the background such that the wavelengths of the at least one laser light source are selected from the group consisting of 3336.8 nanometers (for ethane), 3389 nanometers (for the background), and 3429 nanometers (for methane) with a tolerance of ±1.0 nanometer for each selected wavelength.

6. The system claimed in claim 5, wherein methane, ethane, and the background are detected for natural gas pipeline leaks.

7. The system claimed in claim 3, wherein the gases have absorption wavelengths in the medium wave infrared.

8. The system claimed in claim 1, wherein the system is tunable for detection of hydrocarbon gases.

9. The system claimed in claim 1, wherein the at least one laser light source having a wavelength is tuned to the absorption characteristics of the two or more target fluids.

10. The system claimed in claim 1, wherein the means for signal detection includes an electronic sensor selected from the group consisting of charge coupled device (CCD), complementary metal oxide semiconductor (CMOS), photomultiplier tube, and photodiodes.

11. A method for remote quantitative detection of fluid leaks from a natural gas or oil pipeline by use of an airborne platform; comprising:

a) nearly simultaneously illuminating essentially a same target area of two or more target fluids and a background with at least one laser light source as an illumination source, wherein the two or more target fluids are characterized by two or more absorption wavelengths, and wherein the background has a different wavelength than either of the two or more target fluids;

b) pointing the illumination source relative to a positioning system;

c) scanning for the two or more target fluids in a geometric area along a path using the illumination source;

d) detecting the two or more target fluids using quantitative signal processing;

e) controlling operation of the system;

f) positioning of the airborne platform using path planning and path finding means; and g) communicating presence of the detected leak from the natural gas or oil pipeline.

12. The method claimed in claim 11, wherein the method employs two or more laser light sources.

13. The method claimed in claim 11, wherein the two or more target fluids are gases having absorption characteristics of gases.

14. The method claimed in claim 13, wherein the gases are methane and ethane.

15. The method claimed in claim 14, wherein the at least one laser light source having a wavelength is tuned to the absorption characteristics of methane, ethane, and reflectance characteristics of the background such that the wavelengths of the at least one laser light source are selected from the group consisting of 3336.8 nanometers (for ethane), 3389 nanometers (for the background), and 3429 nanometers (for methane) with a tolerance of ±1.0 nanometer for each selected wavelength.

16. The method claimed in claim 15 wherein methane, ethane, and the background are detected for natural gas pipeline leaks.

17. The method claimed in claim 13, wherein the gases have absorption wavelengths in the medium wave infrared.

18. The method claimed in claim 11, wherein the method is tunable for detection of hydrocarbon gases.

19. The method claimed in claim 11, wherein the at least one laser light source having a wavelength is tuned to the absorption characteristics of the two or more target fluids.

20. The method claimed in claim 1, wherein the means for signal detection includes an electronic sensor selected from the group consisting of charge coupled device (CCD), complementary metal oxide semiconductor (CMOS), photomultiplier tube, and photodiodes.

* * * * *